United States Patent
Bosshart

(10) Patent No.: US 6,273,723 B1
(45) Date of Patent: Aug. 14, 2001

(54) SET OF ARTIFICIAL MOLARS FOR REMOVABLE DENTURES

(76) Inventor: Max Bosshart, Zürichstrasse 5, Einsiedeln (CH)

( * ) Notice: Subject to any disclaimer, the term of this patent is extended or adjusted under 35 U.S.C. 154(b) by 0 days.

(21) Appl. No.: 09/307,096

(22) Filed: May 7, 1999

(30) Foreign Application Priority Data

May 15, 1998 (CH) .................................................. 1085/98

(51) Int. Cl.$^7$ .................................................. A61C 13/08
(52) U.S. Cl. .................................................. 433/197
(58) Field of Search .................................. 433/196, 197, 433/202.1

(56) References Cited

U.S. PATENT DOCUMENTS

| | | | |
|---|---|---|---|
| 990,548 | * | 4/1911 | Gysi ........................ 433/197 |
| 1,657,673 | * | 1/1928 | Gysi ........................ 433/197 |
| 1,677,662 | * | 7/1928 | Sprinkle ................... 433/197 |
| 1,681,436 | * | 8/1928 | Sears ........................ 433/197 |
| 2,006,717 | * | 7/1935 | Phillips ..................... 433/197 |
| 2,115,116 | * | 4/1938 | McGrane ................... 433/197 |
| 2,144,198 | * | 1/1939 | Page ......................... 433/197 |
| 2,203,226 | * | 6/1940 | Klicka ....................... 433/197 |
| 2,617,192 | * | 11/1952 | Goddard .................... 433/197 |
| 2,741,845 | * | 4/1956 | Appenrodt et al. ......... 433/197 |
| 3,027,642 | * | 4/1962 | Strack ....................... 433/197 |
| 3,252,220 | * | 5/1966 | Goddard .................... 433/197 |
| 3,305,926 | | 2/1967 | Gerber . | 
| 4,208,794 | * | 6/1980 | Gerber ...................... 433/197 |
| 4,445,863 | | 5/1984 | Lang et al. . |

FOREIGN PATENT DOCUMENTS

| | | |
|---|---|---|
| 88645 | 3/1921 | (CH) . |
| 109795 | 7/1925 | (CH) . |
| 161975 | 8/1933 | (CH) . |
| 199038 | 10/1938 | (CH) . |
| 405 601 | 7/1966 | (CH) . |
| 607 686 | 10/1978 | (CH) . |
| 1 491 070 | 6/1969 | (DE) . |
| 195 08 762 | 5/1996 | (DE) . |

* cited by examiner

Primary Examiner—Ralph A. Lewis
(74) Attorney, Agent, or Firm—Brown, Martin, Haller & McClain LLP

(57) ABSTRACT

A molar (1) shows a cusp (6), which occludes in a designated central fossa (7). The cusp (6) essentially shows even facets (8,12) of which each facet (9,11) has a coordinating central fossa (7). When biting down, there are at least two coordinating facets of the cusp and the central fossa that meet. At least one set of coordinating facets of the cusp (6) and the central fossa (7) are located outside/buccal (8,9) and/or in the back/distal (24,23) and have essentially a larger-scale surface, than the facets (12,26; 11,27) located in the slope of the opposing ridge. One of the larger facets (8; 9) preferably inclines essentially to the outside and the other one essentially to the back, while the smaller facets, preferably one (12; 11) essentially raises to the inside and the other one essentially to the front. This improves the stability of the denture and provides more space for the tongue.

4 Claims, 2 Drawing Sheets

SET OF ARTIFICIAL MOLARS FOR REMOVABLE DENTURES

BACKGROUND OF THE INVENTION

1. Field of the Invention

The invention relates to a set of prefabricated molars for a set of removable full dentures.

In the dental field, i.e. the technical dental field, prefabricated produced molars are being used with complete full dentures, hybrid dentures and partial dentures and are applied by persons, who are missing some, or all of their teeth. These prefabricated produced molars are being secured and become part of the denture, and together with its synthetic material, forms a solid unit. Such dentures are quite different from crowns and bridges, where the individual molars will be reconstructed completely, meaning they are being constructed in a dental laboratory and will be cemented directly to the previously prepared stump of a tooth.

Hybrid dentures completely cover structures that are located underneath, making securing the dentures to the stumps of the teeth, and through recently invented prefabricated implanted roots (implants) possible, by implementing a push-button-like system. They are, however, with possible exceptions, basically constructed like a normal removable denture, which has prefabricated molars attached to its base.

2. Description of the Prior Art

In the past century, prefabricated molars were made of porcelain and placed in dentures, which had no consequent and specified form relating to their function. Beginning in 1908, A. Gysi developed prefabricated molars, which were strictly constructed according to functional principles. The result of the development currently consists of three different construction types of prefabricated molars, with each clearly defining its functionality, which was actually produced and is still being utilized in the dental field i.e. technical dental field to date. The individual molars are securely anchored in the framework of the denture and have functional contact with the opposing teeth. Each tooth influences the stability of the entire denture and the other teeth of the same denture, since all teeth are securely connected to the framework of the denture. It is therefore important to pay attention to the impact of each individual molar when under the pressure of chewing, as well as the functional impact of all molars together, when constructing the denture. If a denture is to be made at the same time for both, the maxilla and for the mandible, the impact of the reciprocal functionality of the individual molar pairs, as well as all molars together, must be observed.

With "classical" defined type 1 construction (according to A. Gysi; for example compare patents CH-109795, CH-199038 and CH-88645), the molars are equivalent to the shape of the human molars, with perhaps some deviations. They however have no roots but only show the crown of the tooth, which is the part that protrudes from the gum and is visible with natural teeth. In the following description, the term "cusp" or "dental cusp" refers to the conical shaped pointed or rounded eminence on or near the masticating surface of the tooth which occludes with the antagonizing tooth of the opposite dental arch, and the term "fossa" refers to a shallow depression concavity or a hollow depressed area. The oral/palatal cusps of the upper molars which face the tongue, bite in the direction of a central fossa of the lower molars and/or a dental cusp in contact with two opposing teeth, which form central fossa when put together. The buccal cusp of the lower molars, which point toward the cheeks, fit into the central fossa of an upper molar or in the central fossa which was formed by two upper molars and make contact with the outer buccal cusp of the upper molars. The fitting into each central fossa of all cusps is called "classical occlusion".

When moving the mandible, in relation to the maxilla, which is attached to the scull, the cusp of the upper molar forms, stabilized contacts in the shape of gliding surfaces and is therefore essential. According to A. Gysi, all molars of the upper denture shall remain in contact with the lower denture, in order to prevent tipping when the patient moves the mandible. This way the denture will always be supported by a large surface area on both sides (bilateral balancing).

The disadvantage of this type 1 construction is that the functional contact between the outer buccal cusp of the upper and the lower molars very often causes a tipping of the upper and/or the lower denture, when rough and hardly processed bolus is still present. In order to prevent this situation, the molars must be placed in the tongue area, in order for the outer pressure-bearing cusp to be positioned at least in the center of the carrying alveoli ridge, which will however restrict the tongue area considerably. The contact of the outer buccal cusp however may be eliminated, in order to shift the chewing forces inward lingual. The shape and the position of the premolars without bolus being present, makes it impossible or at least very difficult, to stabilize the gliding contact through movements to the side and partially by displacement movements of the mandible, as it is required for the bilateral balancing. Since the molars will be under functional pressure when chewing bolus, the stability of one-sided use is essential. Also between meals and while sleeping, intensive functional contact of the teeth without bolus, will occur.

Resolving the aforementioned disadvantages, molars have been developed according to a construction of type 2 (according to A. Gerber; for example compare patents CH-405601, U.S. Pat. No. 3,305,926 and CH-607686), where the bilateral balancing remains secured and the dentures remain stable and even on the base. That means that they are resting on the appropriate jawbone of the alveoli ridge. For stability reasons the palatal/oral inner upper cusp of the upper molars, which are pointed toward the tongue, are dominantly being used for chewing, in conjunction with the lower central fossa of a molar, or with a central fossa created by two molars. The cusp in this instance, is in general convex-shaped and the appropriate central fossa is in general concave-shaped, so that the molars (in perspective to the upright-positioned denture carrier) create a vertical line of force at a random slant. The outer buccal cusp of the upper molars however do not show any or only show a clearly reduced contact, which is very small and which is located closely near the upper central fossa. The center for chewing and the chewing force are clearly being shifted to the inside (oral), toward the center of the mouth and not to the outside of the upper and lower alveoli ridges, which means not outside the bone structure which carries the masticatory force; since the masticatory forces, which take place outside of the center of the upper and lower alveoli ridges, may cause the denture to tip. The upward outward pressure against the upper and slightly outward-tipped buccal cusp, of the upper molars will completely be deleted or will at least be drastically reduced. This way there is plenty of room for the tongue, without loss of stability by the masticatory force, compared to the construction of type 1. The molar-relief essentially complies with the natural model, however with partially clear deviations.

During a normal and one-sided chewing process, with the bolus being large and hard in the beginning, making the contact of the molars impossible, the outer buccal cusp are not being used. This is called "lingualized occlusion".

During sideways motions of the maxilla, without bolus being present, all molars remain in constant contact with one another (bilateral equilibration balancing), where only the inner palatal molars have contact with the opposing tooth. The upper outer cusp overlap the lower outer cusp, clearly without any contact, since they could make the denture tip when bolus is present.

These molars have the disadvantage, when type 2 construction has been applied that their chewing efficiency is smaller then the chewing efficiency of the molars of the construction type 1. The functionality of the convex-shaped cusp with the concave-shaped central fossa creates a vertical alignment of energies. This is contingent on the fact that the lower tooth must be positioned in this line of force and therefore restricts the space for the tongue.

Combination constructions of type 1 and type 2 are created, when for example a construction by H. P. Foser, which permits the classical occlusions position as in construction type 1, and the lingualized occlusion, like in constructive type 2, and a construction according to H. Schröder (compare for example patent CH-161975) for a molar, where the upper central fossa and the active lower cusps are integrated in the particular denture. This shape is non-anatomical, but is also not flat, like in construction type 3, which follows.

The basic principle of construction type 3 is not to integrate any obstructions for movements of the mandible through a flat chewing surface. The chewing surfaces of the lower molars and/or the upper molars no longer follow the natural molars (non-anatomical molars) but the particular chewing surfaces of such molars are flat. That way, the molars cannot be completely adjusted to the movements of the mandible and cannot be maintained in reciprocal (bilateral) contact. There will always be some loss of contact, whether it is on the inner or outer sides.

With anatomical molded prefabricated molars of the construction types 1 and 2, the oral inner cusp of the molars are situated in the opposite, antagonistic central fossa, in a functional occlusion, where the cusp may be in the molar of the upper denture as well as in the molar of the lower denture and where the appropriate central fossa is either located centered to the opposing tooth, or is formed through two molars, located next to one another. The formation of the cusp and the central fossa create a vector force through their opposing function.

In an ideal situation the central contact function of each set of molars (or also between three molars) of each upper and lower vector force of the occluded molars (left or right side of mouth), meets the center of the supporting alveolar ridge. The alveolar ridge where the natural molars were originally fixed, is the supporting base of the denture for a person without teeth. If the projection of the vector force of the denture from the top and from below, during the masticatory force, is outside the supporting jaw ride, the denture will tip when masticatory force is applied. This applies to an individual molar, as well as to all molars of the denture, when they are under pressure.

Seen from a frontal (transversal) view, the molars of the upper alveoli ridge, compared to the molars of the lower alveoli ridge, are in most cases positioned slightly inward off-center, depending on the degree of the resorption of the jawbone. In order to avoid tipping of the upper denture, the inner cusp or central fossa of the upper molars must ideally be situated vertically under the center of the alveoli ridge. Therefore, depending if the vector force runs vertically, the lower molars with their function center (central fossa or cusp) is located partially considerably within the alveoli ridge. This way, the tongue may be restricted in the area of the lower denture, which will bother the patient while speaking and chewing. To have more room for the tongue, it would be advantageous to divert the vertical vector force in the direction of the lower alveoli ridge, which is located more toward the outside. This means orienting the vector force along the so-called "interalveolar line", which is the imaginary connecting line from the center of the alveoli ridge on top, to the center of the alveoli ridge below, deviated by approximately 10°–15° from the vertical. The molar (in general the lower molar) may be placed out further, buccal toward the alveoli ridge, without effecting the stability of the upper or lower denture.

The side (sagittal) view indicates that the molars, depending on the shape of the alveoli ridge and the degree of resorption of the jaw bones, which carry the denture, stand above a slanted and forward tipping plain, with the higher alveoli ridge naturally rising upward toward the back. Loss of the alveoli ridge can increase this problem considerably. Through the masticatory force, the denture glides forward on this slanted plain. Only through a diversion of the line of force toward the lower back can the molars be made stable for chewing. Only when the vector force meets the mandible ride in the proper angle or at a point and toward the back-oriented angle, is a forward gliding of the lower denture prevented.

An optimal adjustment of the vector force requires type 1 construction, a "classical occlusion" with all of the all cusps fitting into a central fossa. This means, an occlusion of the cusp of the upper molar, pointing orally/palatal toward the tongue, and toward a corresponding central fossa of the lower molars and at the same time an occlusion of the cusp of the lower molars, facing the cheek, toward a corresponding central fossa of the upper molars. It is not possible to direct a given cusp of a given molar in the optimal direction, when the vector force produced by chewing in sideways direction toward the inside/lingual or outward/buccal, as well as in sagittal direction, toward the back/distal or toward the front/mesial, individually or as a combination, and in any case independent of other cusp of that molar. The necessary constructive spacing is missing. The displacement of the lower denture toward the front may be partially avoided by additionally sloping the molar until it is parallel with the supporting alveoli ridge. To achieve this, it is required that the outer buccal cusp are engaging with the lower cusp, otherwise with only the inner cusp occluded with the corresponding central fossa, a diversion of the vector force is not sufficient.

In comparison, construction type 2 does not lead to the correct orientation of the vector force, since the active convex-shaped cusp in the appropriate spherical occluding central fossa, creates a vertical line of force even though both molars are tipped. The outer buccal cusp may not be used for correction of the vector force, since they may not come into contact because they would jeopardize the transversal static.

SUMMARY OF THE INVENTION

It is the task of the presented invention, to suggest an improved construction for construction type 1 or type 2 or a combination of construction types 1 and 2. This new combination will achieve a reorientation of the chewing forces in transversal and in sagittal direction, by using only one cusp in its appropriate central fossa. The controlled diversion of the vector force pertaining to the molars, which are being used for chewing functions, shall be guaranteed for the frontal, as well as for the side views. The transversal and sagittal reorientation of the vector force shall take place without functional implementation of the outer buccal cusp, but shall be achieved with each individual inner oral cusp. If two inner oral cusps have a functional occlusion with an opposing tooth, the diversion of the vector force shall effect each individual cusp or both cusps together.

The solution to this task is a set of prefabricated molars for a removable full denture of the type previously mentioned, which is identified by a combination of features.

The invention as defined in the patent claims will achieve increased space for the tongue and increased chewing stability. By purposely having contacts, designed on a large-scale, between the upper and lower molars in occlusion and by purposely tipping the facets of the upper and lower molars, the resulting vector forces may be tipped in the desired transversal and sagittal direction, alternatively only in transversal or only in sagittal direction or combined in transversal and in sagittal direction. This refers to the projection of the vector forces in one plane, as well as to the frontal (transversal) view and to the side (sagittal) view, and will be achieved by one single occlusion of only one cusp with its matching central fossa. If there are several cusp of one tooth in a functional occlusion, the diversion of the vector forces will be effected by each inner oral cusp individually, or by both inner oral cusp together, without occluding the destabilized outer buccal cusp. This way and in most cases, the chewing forces are much better aligned with the denture-carrying upper and lower alveoli ridge, which will result in a significant improvement of stability of the upper and lower denture. The outer cusp will purposely remain without function. More space for the tongue will remain between the left and the right row of molars, without causing any disadvantage, and the dynamic chewing motions will not be obstructed. In a frontal (transversal) view, a cross-bite is often avoided. In a side (sagittal) view, a better fit of the lower denture, against the slanted alveoli ridge, is achieved and the typical sliding forward of dentures, on a slanted base, when chewing (at least up to a certain angle), can be avoided.

If teeth show more than one active cusp, the desired effect of each individual cusp, or several cusps, may be met.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which.

DESCRIPTION OF THE PREFERRED EMBODIMENT

Figure 1:
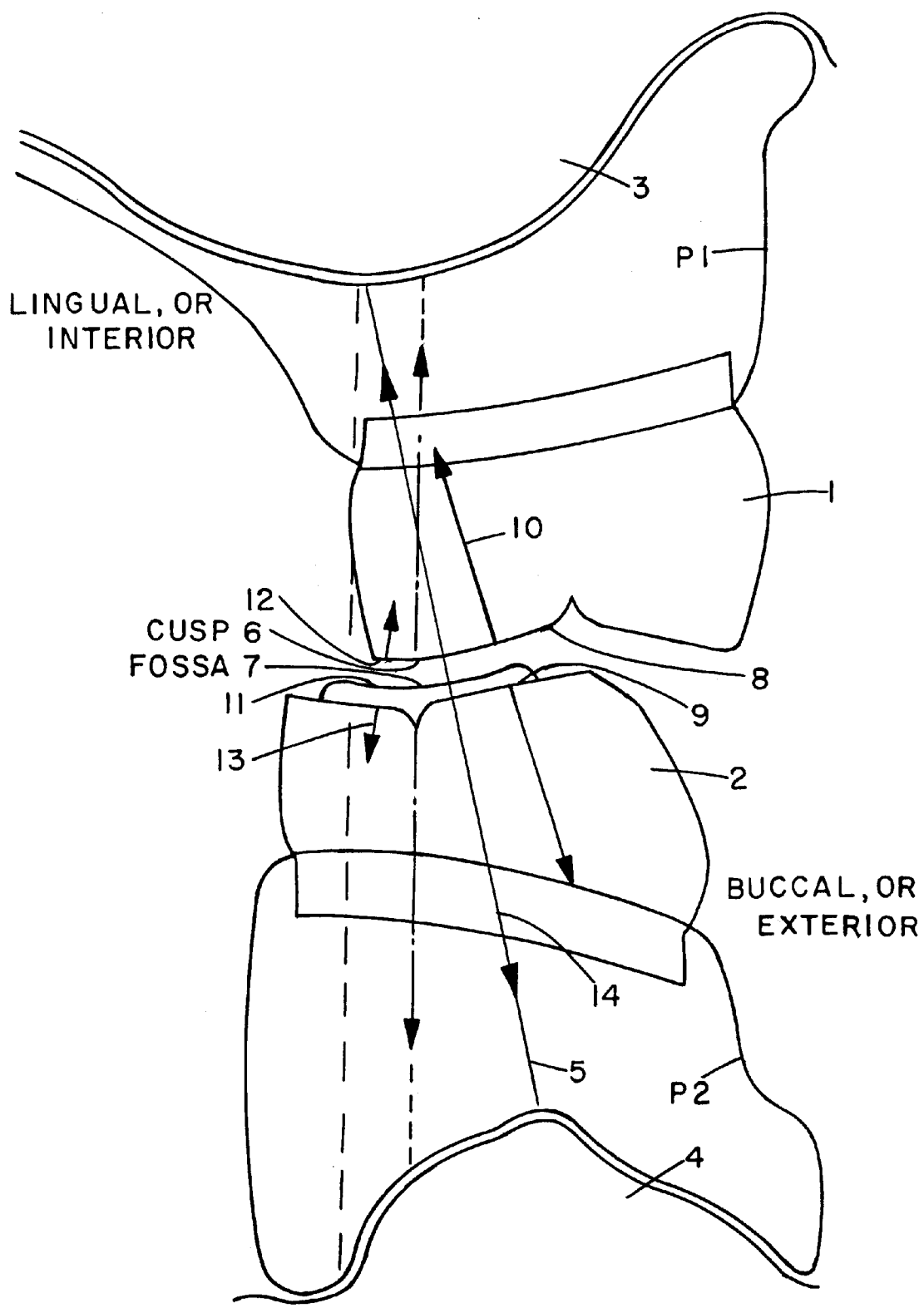
FIG. 1 shows prefabricated molars and an adjoining part of an alveoli ridge in a frontal (transversal) cut-image.
Figure 2:
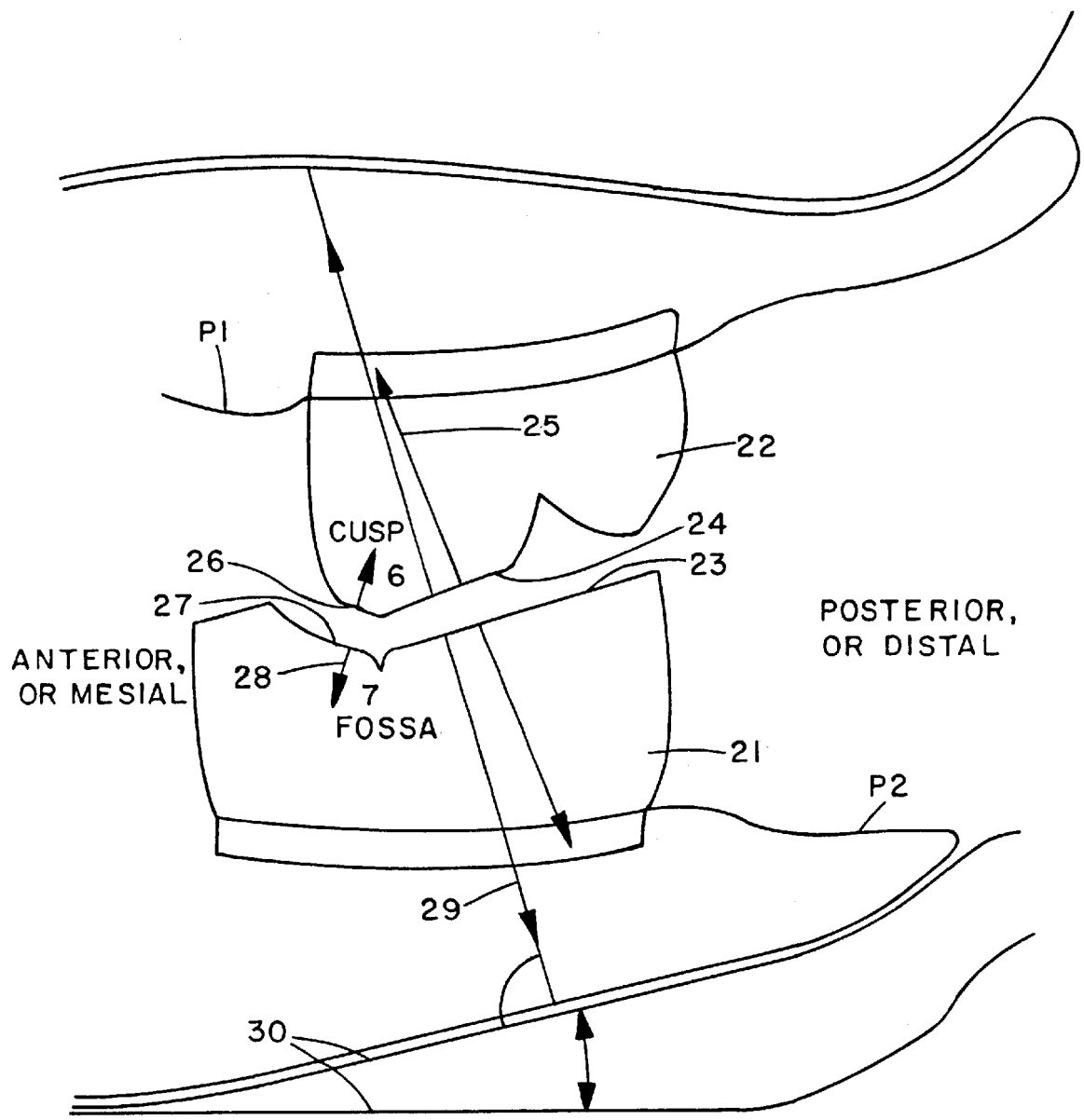
FIG. 2 shows prefabricated molars and an adjoining part of an alveoli ridge of FIG. 1 with a side (sagittal) cut-image.

In the following drawings, however without limitations of the described example of the invention, FIG. 1 reflects a frontal cut-image of an upper prefabricated molar 1 and a lower prefabricated molar 2. Above and below is a classic example of the respective alveoli ridge, marked with 3 and 4. Molars 1 and 2 are of course imbedded in the framework of the denture P1 and P2, which is located between molar 1 and 2 and the corresponding alveoli ridge 3 and 4, and which supports the molar at the corresponding alveoli ridge.

A connecting line 5 connects both alveoli ridges 3 and 4 along the so called "interalveolar line" and shows the desired direction of the real vector force.

A cusp of the upper molar 1 and a central fossa 7 of the lower molar 2, show large-scale and basically even facets, or small plane surfaces, 8 and 9, which are located across from one another. Due to their vertical angle (referring to the upright denture carrier) and their expansion, they create a main vector force 10 of the desired orientation, approximately parallel to the connecting line 5.

To avoid a decline of the lower molar 2, a support facet 11 is considered at the central fossa 7 of the lower molar. This will support the inside (lingual). The contact of a support facet 12, of cusp 6, of the upper molar 1 together with the support facet 11, is almost point-shaped, which means it has a small top surface in order to provide little support as depicted by support vector force 13. The smaller the contact, the smaller the influence of the large-scale contact of the outer facets.

The vector force 14, which is relevant for the stability of the denture, will result from the total sum of both vector forces 10 and 13, and should ideally be oriented parallel to the interalveolar connecting line 5.

The angle of both facets 8 and 9 are designed so that natural movements to the side will not be obstructed, but at the same time they remain as support.

This way a correct transversal centering of the lower molars with the upper molars is assured.

From a side view, the lower molar 21 clearly shows a facet 23, which inclines up toward the back. The back portion of the antagonistic cusp of the upper molar 22 is located next to it with its facets 24 and a wide area of contact. A main vector force 25 is created, which basically runs towards the back (and the upper front) in a right angle to the contact surfaces 23 and 24. In order to prevent losing control and displacement of both molars to one another, a small help contact of help facets 26 and 27, of upper and lower molars 22 and 21, which point in the opposite direction of the large contact areas, is necessary. The smaller this help contact or help facet 26 and 27 and the help vector force 28, which created this is, the smaller the effectiveness of the wide area of contact and the effect of the rear facets 23 and 24. The vector force 29, as a result of both vector forces 25 and 28, is relevant for the stability of the denture. If the resulting vector force 29 meets the supporting alveoli ridge with less than 90°, the denture 30 will not try to slide away toward the front.

The two facets 8 and 24 with a wide area of contact, and the two supporting facets 12 and 26 of the cusp 6 on one side, and the two facets 9 and 23 with a wide area of contact, and the two supporting facets 11 and 27 on the other side, are positioned and dimensioned in a way that they will meet at one point. That way, the resulting vector force is essentially oriented in the direction of the interalveolar connecting line 5 of molars 1 and 22, as well as molars 2 and 21 of cusp 6 and the central fossa 7.

This way correct sagittal centering of the lower molars to the upper molars is being secured.

Both corrections of the vector forces (transversal and sagittal) as described, may be applied individually or combined with several molars, depending on the requirements of the circumstances. They may be used the same way and at the same time for molars, for premolars and even for front teeth. The central fossa may be centrally-located in a molar or may be formed by two molars. A molar may have several connections between cusp and central fossa of that shape, such as with molars with two oral (inner) cusps.

Using the same principle, and depending on the requirements of individual cases, it is possible to reach a correction of the vector forces which are pointed in the opposite direction of the previously-described correction of the vector forces, which means in an upper-outward and/or lower-front direction.

With this invention it is possible to specifically control and improve the vector forces of a vertical mode of operation (construction of type 2) or even statically incorrect placement (construction of type 1). In addition to improving the stability of the denture, more space for the tongue is being created.

Although a preferred embodiment of the invention has been described above by way of example only, it will be understood by those skilled in the field that modifications may be made to the disclosed embodiment without departing from the scope of the invention, which is defined by the appended claims.

I claim:

1. An artificial molar assembly for embedding in a wearer's removable artificial denture and adapted to be supported at a gum ridge of the wearer via a denture body, the assembly comprising:

at least two opposing molars, a first of the molars having at least one cusp and a second of the molars defining at least part of a fossa, whereby the cusp engages the fossa formed on the opposing second molar or formed cooperatively between the second molar and at least one additional molar;

the cusp and the fossa each having essentially flat pairs of corresponding facets which are adapted to come to rest on each other when the corresponding cusp and fossa engage one another;

wherein at least a first pair of corresponding, opposed facets of the cusp and fossa comprises a first facet on the first molar and a second facet on the second molar, the first and second facets having the same orientation and respective locations with respect to the denture, the first facet being located on the exterior side of the cusp and the second facet being located on the exterior side of the denture;

the facets including additional facets oriented differently from said first pair of opposed facets; and the first pair of opposed facets being of a predetermined area that is larger than a corresponding area of said additional, differently oriented facets.

2. An artificial molar assembly for embedding in a wearer's removable artificial denture and adapted to be supported at a gum ridge of the wearer via a denture body, the assembly comprising:

at least two opposing molars, a first of the molars having at least one cusp and a second of the molars defining at least part of a fossa, whereby the cusp engages the fossa formed on the opposing second molar or formed cooperatively between the second molar and at least one additional molar;

the cusp and the fossa each having essentially flat pairs of corresponding facets which are adapted to come to rest on each other when the corresponding cusp and fossa engage one another;

wherein at least a first pair of corresponding, opposed facets of the cusp and fossa comprises a first facet on the first molar and a second facet on the second molar, the first and second facets having the same orientation and respective locations with respect to the denture, the first facet being located on the posterior side of the cusp and the second facet being located on the posterior side of the denture;

the facets including additional facets oriented differently from said first pair of opposed facets; and the first pair of opposed facets being of a predetermined area that is larger than a corresponding area of said additional, differently oriented facets.

3. An artificial molar assembly for embedding in a wearer's removable artificial denture and adapted to be supported at a gum ridge of the wearer via a denture body, the assembly comprising:

at least two opposing molars, a first of the molars having at least one cusp and a second of the molars defining at least part of a fossa, whereby the cusp engages the fossa formed on the opposing second molar or formed cooperatively between the second molar and at least one additional molar;

the cusp and the fossa each having essentially flat pairs of corresponding facets which are adapted to come to rest on each other when the corresponding cusp and fossa engage one another;

wherein at least a first pair of corresponding, opposed facets of the cusp and fossa comprises a first facet on the first molar and a second facet on the second molar, the first and second facets having the same orientation and respective locations with respect to the denture, the first facet being located on both the exterior and the posterior side of the denture;

the facets including additional facets oriented differently from said first pair of opposed facets; and the first pair of opposed facets being of a predetermined area that is larger than a corresponding area of said additional, differently oriented facets.

4. A set of artificial molars according to any one of claims 1–3, comprising:

two pairs of larger area facets wherein one pair of larger area facets are oriented so that the facets are inclined sidewards with respect to the denture and the other pair of large area facets are oriented so that the facets are inclined backwards with respect to the denture;

and two pairs of smaller area facets wherein one pair of the smaller area facets is oriented so that the facets are inclined inward with respect to the denture and the other pair of small area facets is oriented so that the facets incline forward with respect to the denture.

* * * * *